United States Patent
Flores et al.

(10) Patent No.: US 10,596,353 B2
(45) Date of Patent: Mar. 24, 2020

(54) MRI-COMPATIBLE GUIDEWIRE

(71) Applicant: MRI Interventions, Inc., Irvine, CA (US)

(72) Inventors: Jesse Flores, Perris, CA (US); Rajesh Pandey, Irvine, CA (US); Peter Piferi, Orange, CA (US); Kamal Vij, Chandler, AZ (US)

(73) Assignee: MRI Interventions, Inc., Irvine, CA (US)

( * ) Notice: Subject to any disclaimer, the term of this patent is extended or adjusted under 35 U.S.C. 154(b) by 237 days.

(21) Appl. No.: 15/294,013

(22) Filed: Oct. 14, 2016

(65) Prior Publication Data
US 2017/0106171 A1 Apr. 20, 2017

Related U.S. Application Data (60) Provisional application No. 62/242,001, filed on Oct. 15, 2015.

(51) Int. Cl.
*A61M 25/09* (2006.01)

(52) U.S. Cl.
CPC ... *A61M 25/09* (2013.01); *A61M 2025/09083* (2013.01); *A61M 2025/09133* (2013.01)

(58) Field of Classification Search
CPC ............ A61M 25/09; A61M 25/09025; A61M 25/01; A61B 5/055
See application file for complete search history.

(56) References Cited

U.S. PATENT DOCUMENTS

| | | | | |
|---|---|---|---|---|
| 4,779,628 A | * | 10/1988 | Machek | A61M 25/09025 600/434 |
| 5,040,543 A | * | 8/1991 | Badera | A61M 25/09025 600/434 |
| 5,211,636 A | * | 5/1993 | Mische | A61M 25/09 600/585 |
| 5,259,393 A | * | 11/1993 | Corso, Jr. | A61B 6/12 600/585 |
| 6,139,540 A | * | 10/2000 | Rost | A61M 25/09 600/585 |

(Continued)

OTHER PUBLICATIONS

Ergin Atalar; 'Radiofrequency Safety for Interventional MRI Procedures' Acad Radiol 2005; 12:1149-1157.*

*Primary Examiner* — Patrick Fernandes
(74) *Attorney, Agent, or Firm* — Myers Bigel, P.A.

(57) ABSTRACT

A passive MRI-compatible guidewire includes an elongate, flexible tubular shaft, an elongate core wire of non-ferromagnetic material, and an elongate spring coil of non-ferromagnetic material axially surrounding the elongate core wire to form a distal end portion. The core wire includes opposite first and second end portions separated by an intermediate portion. The intermediate portion has a round cross-section, and the first and second end portions each have a non-round cross-section. The first end portion of the core wire resides within an inner lumen of the tubular shaft and is secured therewithin. The spring coil includes opposite first and second ends, and the spring coil second end is secured to the core wire second end portion via polymeric material that forms a rounded distal tip of the guidewire. The guidewire includes a plurality of spaced-apart, passive MRI-visible markers.

21 Claims, 3 Drawing Sheets

(56) References Cited

U.S. PATENT DOCUMENTS

| | | | |
|---|---|---|---|
| 2001/0016962 A1* | 8/2001 | Moore | B08B 9/00 |
| | | | 15/104.16 |
| 2004/0167436 A1* | 8/2004 | Reynolds | A61M 25/09 |
| | | | 600/585 |
| 2004/0167439 A1* | 8/2004 | Sharrow | A61M 25/09 |
| | | | 600/585 |
| 2005/0070793 A1* | 3/2005 | Pacetti | A61M 25/09 |
| | | | 600/431 |
| 2012/0053572 A1* | 3/2012 | Rusu | A61B 5/055 |
| | | | 606/1 |
| 2013/0289533 A1* | 10/2013 | Duering | A61L 29/126 |
| | | | 604/529 |
| 2014/0081244 A1* | 3/2014 | Voeller | A61M 25/01 |
| | | | 604/528 |

* cited by examiner

MRI-COMPATIBLE GUIDEWIRE

RELATED APPLICATION

This application claims the benefit of and priority to U.S. Provisional Patent Application No. 62/242,001 filed Oct. 15, 2015, the disclosure of which is incorporated herein by reference as if set forth in its entirety.

GOVERNMENT FUNDING

This invention was made, in-part, with United States government support under grant number HHSN268201400048C from the National Institutes of Health. The United States government has certain rights to this invention.

FIELD OF THE INVENTION

The present invention relates generally to medical devices and, more particularly, to MRI-guidable guidewires.

BACKGROUND

Many percutaneous intravascular procedures use a guidewire as an initial approach of accessing a particular vessel. Once the distal guidewire tip has been placed at the area of interest, a catheter is passed over the wire from the proximal end using it as a guide to track the catheter into that vessel. Conventional intravascular procedures are conducted using X-ray and/or ultrasound imaging technology to facilitate catheter guidance.

Magnetic resonance imaging (MRI) has several distinct advantages over X-ray imaging technology, such as excellent soft-tissue contrast, the ability to define any tomographic plane, and the absence of ionizing radiation exposure. In addition, MRI offers several specific advantages that make it especially well suited for guiding various devices used in diagnostic and therapeutic procedures including: 1) real-time interactive imaging, 2) direct visualization of critical anatomic landmarks, 3) direct high resolution imaging, 4) visualization of a device-tissue interface, 5) the ability to actively track device position in three-dimensional space, and 6) elimination of radiation exposure.

Induced RF currents (referred to as RF coupling) on guide wires and other elongated devices utilized in MRI environments can be problematic. Such RF coupling may cause significant image artifacts, and may induce undesired heating and cause local tissue damage. To reduce the risk of tissue damage, it is desirable to reduce or prevent patient contact with cables and other conductive devices in an MRI environment. Such contact, however, may be unavoidable in some cases. For devices that are inserted inside the body, such as intravascular devices, the risk of tissue damage may increase.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a passive MRI-compatible guidewire includes an elongate, flexible tubular shaft, an elongate core wire of non-ferromagnetic material, and a longitudinally extending spring coil of non-ferromagnetic material axially surrounding a portion of the core wire to form a shapeable distal end portion. The guidewire is designed such that the guidewire and surrounding tissue warm up less than less than 2° C. at 1 Watt/kilogram maximum specific absorption rate (SAR) in an MRI environment at 1.5 Tesla. In some embodiments the guidewire may have an outer diameter of less than or equal to about 0.035 inch, and may have a length of between about 2 meters and about 3 meters.

In some embodiments, the elongate core wire is formed from a shape memory or super elastic alloy such as Nitinol, and the spring coil is formed from tungsten. In some embodiments, the elongate tubular shaft is formed from polyether ether ketone (PEEK). As known to those skilled in the art of MRI, Nitinol is non-ferromagnetic nickel-titanium alloy with a lower magnetic susceptibility than conventional stainless steel.

The elongate core wire includes opposite first and second end portions separated by an intermediate portion. The intermediate portion has a round cross-section, and the first and second end portions each have non-round cross-sections (e.g., a flattened or ribbon-shaped configuration). The first end portion of the elongate core wire resides within an inner lumen of the tubular shaft and is secured therewithin. The spring coil includes opposite first and second ends, and the spring coil second end is secured to the elongate core wire second end portion.

The guidewire can include a transition section between a distal end of the elongate tubular shaft and the distal end portion. The transition section includes an elongate inner tube and an elongate outer tube, each having respective opposite first and second end portions. In some embodiments, the inner tube is formed from polyimide, and the outer tube is formed from polyether block amide. The inner tube first end portion is inserted within the lumen of the tubular shaft at the tubular shaft distal end, and the outer tube coaxially surrounds and is secured to the inner tube second end portion. The spring coil first end resides within a lumen of the outer tube at the outer tube second end and surrounds a portion of the inner tube second end. The elongate core wire extends through a lumen of the inner tube and the first end thereof is secured within a fused silica capillary tube that is located within the lumen of the tubular shaft.

The spring coil second end is secured to the elongate core wire second end portion via polymeric material that forms an external rounded distal tip of the guidewire. An exemplary polymeric material is an epoxy resin. In some embodiments, a distal portion of the core wire second end is bent about one hundred eighty degrees (180°) and provides an anchor point for the spring coil.

The guidewire can include a plurality of spaced-apart, passive MRI-visible markers that are visible in an MRI as they generate MRI image data signals. For example, the core wire second end portion includes a plurality of these spaced-apart MRI-visible markers that allow the position of the distal tip of the guidewire to be determined within the body of a subject and relative to a 3-D coordinate system of an MRI scanner. In some embodiments, the MRI-visible markers can be a mixture of adhesive and iron oxide nanoparticles, such as at a ratio of about 0.1 gram of iron oxide nanoparticles per gram of adhesive. It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

DETAILED DESCRIPTION

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The term "about", as used herein with respect to a value or number, means that the value or number can vary by +/−twenty percent (20%).

The term "lumen", as used herein, denotes the space enclosed by a tube-like structure.

The terms "MRI or MR Scanner" are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio.

The term "RF safe" means that an intravascular device, such as the guidewire of the present invention, is configured to operate safely when exposed to RF signals, particularly RF signals associated with MRI systems, without inducing unplanned current that inadvertently unduly heats local tissue or interferes with the planned therapy. The term "MRI visible" means that the device, or one or more portions thereof, is visible, directly or indirectly, in an MRI image. The visibility may be indicated by the increased SNR of the MRI signal proximate the device. The device can act as an MRI receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T (Tesla), typically above 1.0 T, and more typically between about 1.5 T and 10 T. Embodiments of the invention may be particularly suitable for 1.5 T and/or 3.0 T systems.

The term "shapeable", as used herein, means capable of being at least somewhat deformed. As discussed below, the distal section 40 of the guidewire 10 of the present invention is shapeable in order to facilitate steering of the guidewire 10 through the body of a subject.

Embodiments of the present invention can be configured to guide and/or place medical devices such as diagnostic or interventional devices in an MRI environment (e.g., interventional medical suite) to any desired internal region of a subject of interest, including, in some embodiments, to a cardiac location. The subject can be animal and/or human subjects.

Figures 1, 2:
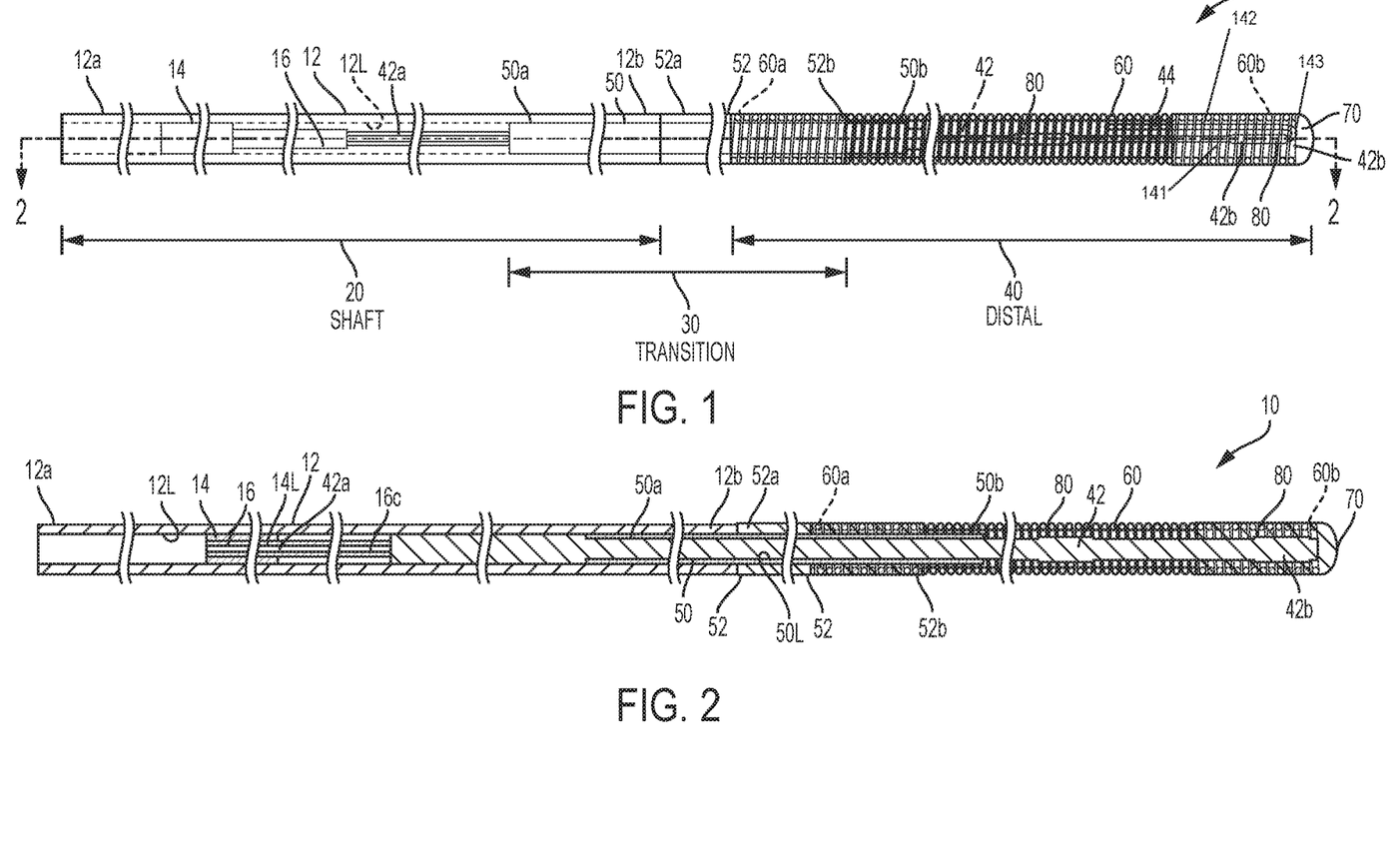
FIG. 1 is a side view of a passive MRI-compatible guidewire with some of the outer surfaces thereof removed to better illustrate the various internal components, according to some embodiments of the present invention.
FIG. 2 is a cross-sectional view of the guidewire of FIG. 1 taken along lines 2-2 in FIG. 1.

Referring now to FIGS. 1 and 2, an RF-safe and passive guidewire 10 for use in an MRI procedure is illustrated. The term "passive guidewire" as used herein means that the guidewire 10 is not electrically connected to an MRI scanner circuit or RF coil. The guidewire 10 is constructed from nonmagnetic materials in order to operate safely inside the strong magnetic field of an MRI scanner, and the guidewire 10 is configured such that the guidewire 10 and surrounding tissue warm up less than less than 2° C. at 1 Watt/kilogram maximum specific absorption rate (SAR) in an MRI environment at 1.5 Tesla. The guidewire 10 can have a smooth outer surface to facilitate sliding other intravascular devices, such as catheters, etc., over the guidewire 10.

The guidewire 10 is flexible and steerable and, for ease of discussion, can be described as having three sections: a shaft section 20, a transition section 30, and a distal tip section 40, as illustrated in FIG. 1. The transition section 30 overlaps a portion of the shaft and distal tip sections 20, 40, as illustrated. In some embodiments, the guidewire 10 has an outer diameter that is less than or equal to 0.035 inch, and has a length of between about 2 meters and about 3 meters. However, other outer diameters and lengths are possible.

The shaft section 20 includes an elongate, flexible tubular shaft 12 having an inner lumen 12L. The shaft 12 comprises the majority of the overall length of the guidewire 10 and is formed from a nonconductive material such as polyether ether ketone (PEEK), although other materials may be utilized. The shaft 12 is reinforced with an elongate capillary tube 14 of a rigid material, such as fused silica, located within the shaft lumen 12L. Another capillary tube 16 is located inside the capillary tube 14 and extends further toward the distal end of the guidewire 10. The inner capillary tube 16 provides a smooth transition into the distal tip section 40 of the guidewire 10. In some embodiments, the outer capillary tube 14 extends to approximately 4.6" from the distal end of the outer tube 52, or 6.9" from the distal tip of the guidewire 10. The inner capillary tube 16 extends to approximately 3.6" from the distal end of the outer tube 52, or 5.9" from the distal tip of the guidewire 10.

This PEEK shaft/fused silica tube combination provides rigidity for pushing and allows for torque transfer during manipulation of the guidewire 10 in use. Moreover, since PEEK and fused silica are both electrical insulators, they do not cause any increase in tissue heating when used inside an MRI scanner. The PEEK material of the shaft 12 also serves as a safety barrier, in case the fused silica capillary tube 14 were to break. The fused silica capillary tube includes an inner lumen that is filled with adhesive to further enhance the strength and rigidity of the guidewire shaft 12. In some embodiments, the adhesive is applied along the entire length of the outer capillary tube 14.

Figure 3:
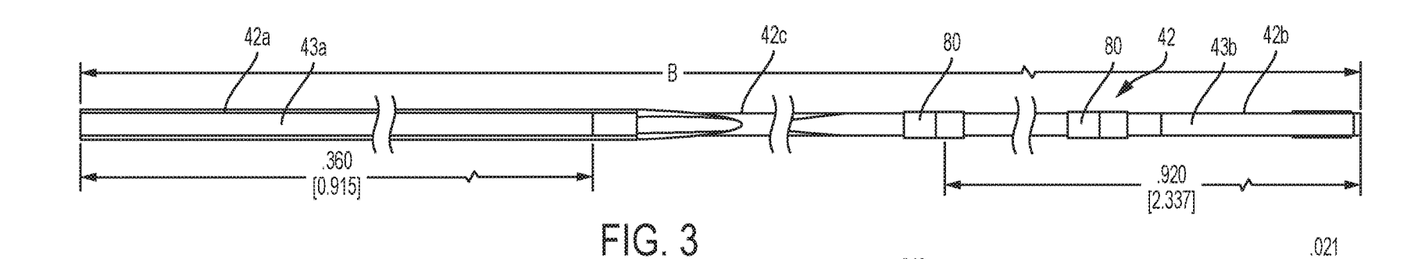
FIG. 3 is a plan view of the elongate core wire in the guidewire of FIGS. 1-2, according to some embodiments.
Figure 4:
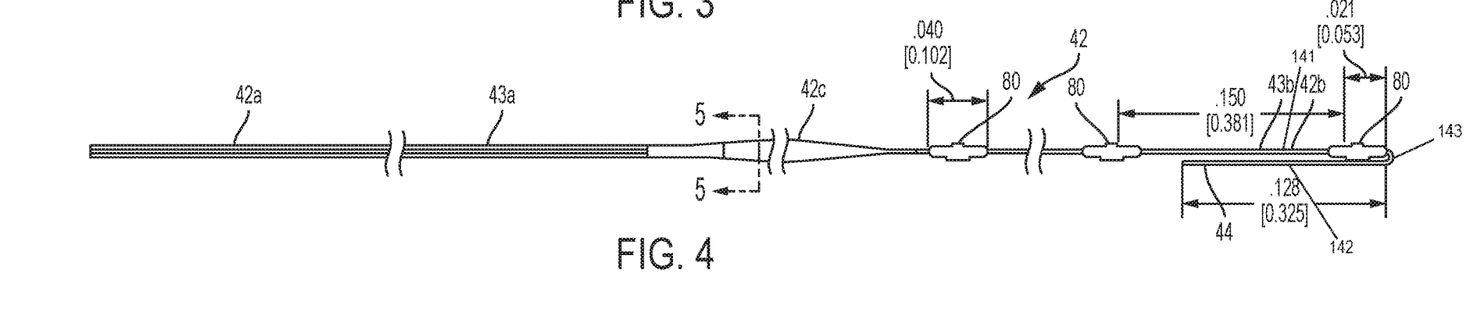
FIG. 4 is a side view of the elongate core wire of FIG. 3.
Figure 5:
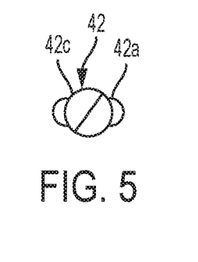
FIG. 5 is a cross-sectional view of the elongated wire of FIG. 4 taken along lines 5-5 in FIG. 4.

The distal section 40 of the guidewire 10 is atraumatic and shapeable to facilitate steering through the body of a subject without causing injury to the subject. An elongate core wire 42 of non-ferromagnetic material, such as Nitinol, is the backbone of the transition and distal tip sections 30, 40. Referring also to FIGS. 3-5, the elongate core wire 42 includes opposite first and second end portions 42a, 42b separated by an intermediate portion 42c. The intermediate portion 42c has a round cross-section (FIG. 5), and the first and second end portions 42a, 42b each have a non-round or flattened configuration. In other words, the first and second end portions 42a, 42b form ribbon-shaped or flattened sections or regions 43a, 43b. In some embodiments, one or both of the second end portions 42a, 42b have a non-round configuration with laterally extending projections. However, various non-round configurations may be utilized. An exemplary maximum outer diameter of the intermediate portion 42c is about 0.014 inch.

The flattened region 43b allows for a smooth transition from the shaft 12 to the distal tip section 40 of the guidewire 10 and can prevent the guidewire 10 from "kinking" during use. As illustrated in FIG. 4, the distal most portion 44 of the elongated wire second end 42b is bent about one hundred eighty degrees (180°) to reside parallel to an adjacent segment for a length at the distal tip section. This bent shape can provide an anchor point for the spring coil 60, as described below. The ribbon-shaped region 43a at the first end portion 42a of the core wire 42 can provide an anchor point for securing the core wire 42 to the inside of the tubular shaft 12.

Referring back to FIGS. 1 and 2, the transition section 30 of the guidewire 10 includes an elongate inner tube 50 and an elongate outer tube 52. The inner tube 50 includes opposite first and second end portions 50a, 50b and the outer tube includes opposite first and second end portions 52a, 52b. In some embodiments, the inner tube 50 is formed from polyimide, and the outer tube is formed from polyether block amide (PEBA), however, other materials may be utilized. PEBA is a thermoplastic elastomer (TPE). Exemplary PEBA that may be used in accordance with embodiments of the present invention includes PEBAX® available from the Arkema Group, and VESTAMID® E available from Evonik Industries. The inner tube first end portion 50a can reside within the lumen 12L of the tubular shaft 12 at the tubular shaft distal end 12b. As illustrated, the outer tube 52 coaxially surrounds and is secured to the inner tube second end portion 50b, as illustrated in FIG. 2.

An elongate (helical) spring coil 60 of non-ferromagnetic material axially surrounds the second end portion of the core wire 42, and includes opposite first and second ends 60a, 60b. The spring coil first end 60a resides within a lumen 52L of the outer tube 52 at the outer tube second end 52b, and the spring coil 60 surrounds a portion of the inner tube second end 50b, as illustrated in FIG. 2. The core wire 42 extends through a lumen 50L of the inner tube 50 and is secured to the shaft 12, as described below. In some embodiments, the spring coil 60 is formed from tungsten, however other non-ferromagnetic materials may be utilized. The coils of the spring coil are arranged tightly together such that adjacent coils are in contacting relationship. The coils are configured to touch or substantially touch when the tip is bent. For example, when the tip of the guidewire 10 is bent, the coils touch on the compressive side of the bend and would touch on the tensile side, except for perhaps the top of the curve.

The core wire 42 and spring coil 60 form the shapeable distal tip section 40 of the guidewire 10, as illustrated in FIG. 1. The outer tube 52 can maintain a constant outside diameter relative to the shaft section 20 while providing a gradual transition between the shaft section 20 and the distal tip section 40. The inner tube 50 provides the outer tube 52 and the spring coil 60 a stable bonding surface without compromising the smooth bend of the core wire 42 during use. The spring coil 60 does not inhibit smooth bending of the core wire 42 during use.

Figures 7, 8, 9:
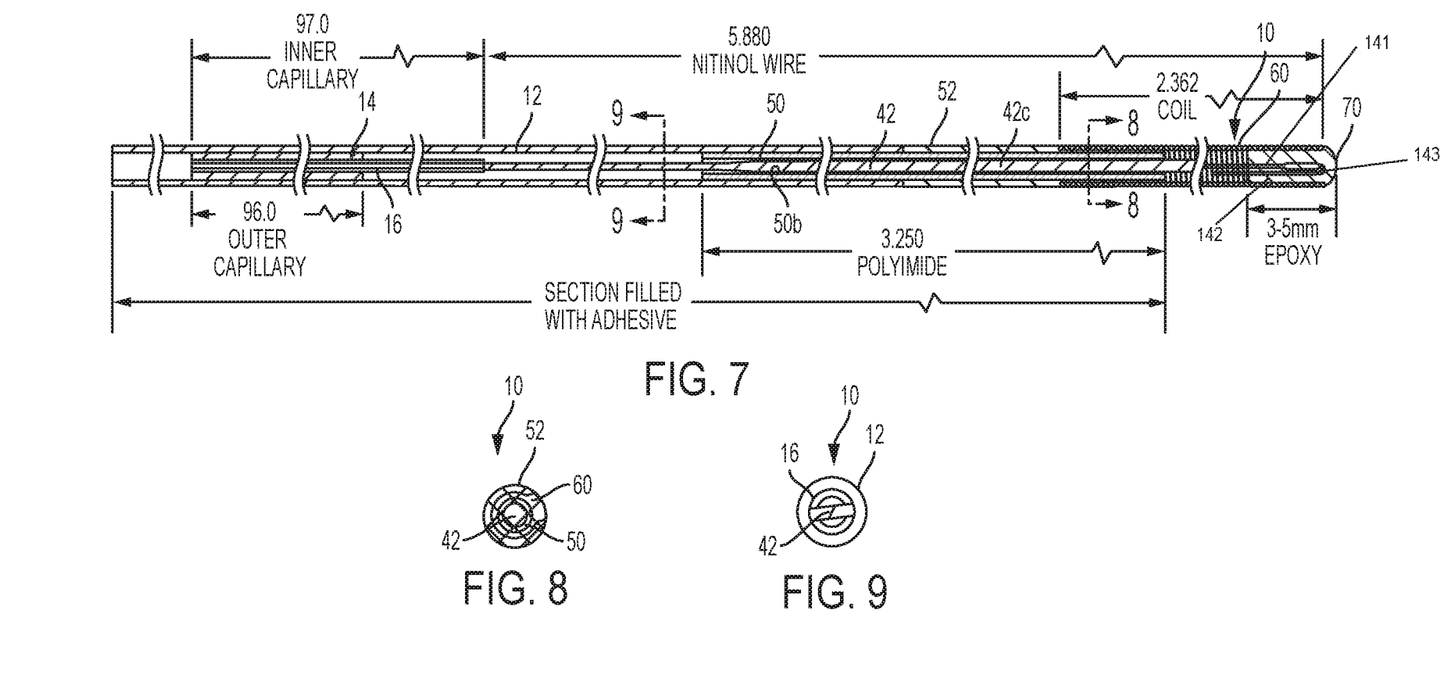
FIG. 7 is cross-sectional view of the guidewire of FIG. 6 taken along lines 7-7 in FIG. 6.
FIG. 8 is cross-sectional view of the guidewire of FIG. 7 taken along lines 8-8 in FIG. 7.
FIG. 9 is cross-sectional view of the guidewire of FIG. 7 taken along lines 9-9 in FIG. 7.

The spring coil second end 60b is secured to the core wire second end portion 42b via polymeric material that also forms a rounded distal tip 70 of the guidewire 10. An exemplary polymeric material for securing the spring coil 60 to the elongated wire 42 is epoxy resin. As illustrated in FIGS. 1, 4 and 7, the one hundred eighty degree (180°) bend of the distal most portion 44 of the core wire second end 42b facilitates securing the second end 60b of the spring coil 60 via epoxy resin, because the bent distal portion 44 provides additional surface area for the epoxy resin to adhere to. The illustrated one hundred eighty degree(180°) bend of the distal most portion 44 of the core wire second end 42b defines a bent tip 143 joining first and second legs 141, 142, respectively. As shown, the first and second legs 141, 142 reside inside the second end 60b of the spring coil. The bent distal portion 44 creates a mechanical interlock with the epoxy since epoxy will flow all around the bend and then harden around it. This bend creates an anchor feature.

The first end 42a of the core wire 42 is secured within the lumen 12L of the elongated shaft 12. For example, as illustrated in FIGS. 1 and 2, the first end 42a of the core wire 42 is secured (e.g., adhesively secured) within a lumen 16L of an elongate fused silica capillary tube 16. This fused silica capillary tube 16 is secured (e.g., adhesively secured) within a lumen 14L of another elongate capillary tube 14. This second elongated capillary tube 14 is secured (e.g., adhesively secured) within the lumen 12L of the elongated shaft 12. In some embodiments, adhesive fills the inner lumens and spaces in between the capillary tubes 14, 16.

Referring to FIGS. 1-3, the core wire 42 includes a plurality of spaced-apart passive MRI-visible markers 80. The passive MRI-visible markers 80 can be elongate as shown. Although only illustrated at the second end portion 42b of the core wire 42, passive MRI-visible markers may be provided at various other locations of the core wire 42, as well as other portions of the guidewire 10. As would be understood by one of skill in the art of the present invention, the passive MRI markers 80 are visible in an MRI as they generate MRI image data signals, but use no wires or circuitry. The passive MRI markers 80 are not electrically connected to an MRI scanner circuit or RF coil. The passive MRI markers 80 can be formed from material that contains nuclei with their own distinct signal that is different from water or fat. When exposed to MRI, the position of the passive MRI markers 80 and, thus, the distal tip section 40 of the guidewire 10 can be determined within the body of a subject and relative to the 3-D coordinate system of an MRI scanner. In some embodiments, the passive MRI markers 80 can comprise a material that does not provide any signal (i.e., shows as a dark spot in an MR image).

In one embodiment, the passive MRI markers 80 comprise adhesive and iron oxide nanoparticles that are applied directly or indirectly to the core wire 42. Higher magnetic susceptibility of iron oxide particles creates distortion in the $B_0$ field of an MRI magnet. These distortions appear as voids in MRI images, and the size of the void depends on the nanoparticles/adhesive ratio in the mixture. Exemplary iron oxide nanoparticles that may be utilized are available from U.S. Research Nanomaterials, Inc., Houston, Texas. An exemplary adhesive that may be utilized is Loctite® 3311™, although other adhesives may be utilized. an exemplary mixture of adhesive and iron oxide nanoparticles may be at a ratio of about 0.1 gram of iron oxide nanoparticles per gram of adhesive.

Figure 6:
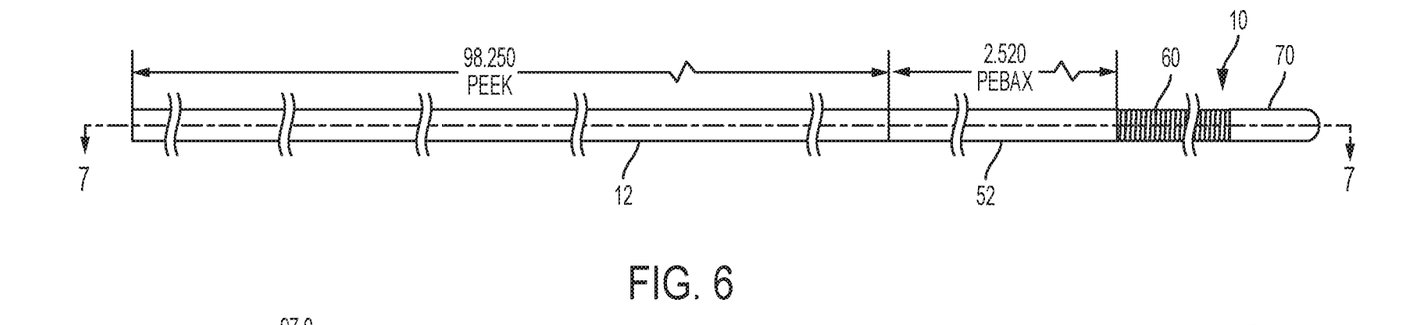
FIG. 6 is a side view of the guidewire of FIG. 1, but with all of the external surfaces illustrated.

FIG. 6 is an outer view of an embodiment of the guidewire 10 of FIGS. 1-2 that illustrates the various external (exposed) materials. The elongate shaft 12, typically comprising PEEK material, extends to the outer tube 52. The spring coil 60 extends from the outer tube 52 and is secured to the core wire 42 (not shown in FIG. 6) via epoxy resin 70. FIGS. 7-9 are various cross-sectional views of the guidewire 10 of FIG. 7. For example, FIG. 8 is a cross-sectional view illustrating the intermediate portion of the core wire extending through the inner polyimide tube 50, which is surrounded by the outer tube 52 and coil 60. FIG. 9 is a cross-sectional view illustrating the core wire secured within the inner fused silica capillary tube 16 within the tubular shaft 12.

Table 1 below illustrates a range of lengths and dimensions for the guidewire 10 and the various components thereof.

TABLE 1

|  | Exemplary (inches) | Minimum (inches) | Maximum (inches) |
| --- | --- | --- | --- |
| Length of Guidewire 10 | 103.1 | 43 | 127 |
| Diameter of Guidewire 10 | 0.034 | 0.01 | 0.06 |
| Length of Distal Tip of Spring Coil 60 | 2.363 | 1 | 8 |
| Length of Core Wire 42 | 5.880 | 2 | 10 |
| Length of Tubular Shaft 12 | 98.25 | 33 | 105 |
| Length of Fused Silica Tube 16 | 97 | 32 | 104 |
| Length of Fused Silica Tube 14 | 96 | 31 | 103 |
| Length of Inner Tube 50 | 2.520 | 1 | 10 |

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A MRI-compatible guidewire, comprising:
an elongate, flexible tubular shaft comprising an inner lumen;
an elongate core wire of non-ferromagnetic material comprising opposite first and second end portions separated by an intermediate portion, wherein the intermediate portion has a round cross-section, and wherein the first and second end portions each have a non-round cross-section, and wherein the first end portion extends into the inner lumen of the elongate, flexible tubular shaft and is adhesively secured therewithin; and an elongate spring coil of non-ferromagnetic material axially surrounding a portion of the elongate core wire, wherein the elongate spring coil comprises opposite first and second ends, wherein a distal portion of the elongate core wire second end portion comprises a first leg that merges into a bent tip that is bent about one hundred eighty degrees (180°) that merges into a second leg that resides adjacent the first leg of the elongate core wire, wherein the second leg comprises an end facing the intermediate portion of the elongate core wire, wherein the first and second legs of the distal portion of the elongate core wire reside inside the elongate spring coil, wherein the second end of the elongate spring coil is anchored directly to the first and second legs of the second end portion of the elongate core wire via polymeric material, and wherein the elongate core wire and the elongate spring coil form a distal end portion of the guidewire.

2. The MRI-compatible guidewire of claim 1, wherein the polymeric material forms an external rounded distal tip of the guidewire, and wherein the first and second legs are parallel to each other.

3. The MRI-compatible guidewire of claim 2, wherein the polymeric material comprises an epoxy resin.

4. The MRI-compatible guidewire of claim 1, wherein the elongate core wire comprises Nitinol, and wherein the elongate spring coil comprises tungsten.

5. The MRI-compatible guidewire of claim 1, wherein the second end portion of the elongate core wire comprises a plurality of elongate spaced-apart passive MRI-visible markers with one of the elongate spaced apart passive MRI-visible markers configured to define an enlarged outer diameter of the first leg of the elongate core wire adjacent and before the bent tip.

6. The MRI-compatible guidewire of claim 5, wherein each of the passive MRI-visible markers comprises iron oxide nanoparticles.

7. The MRI-compatible guidewire of claim 6, wherein the iron oxide nanoparticles are provided as a mixture of adhesive and iron oxide nanoparticles in a ratio of about 0.1 gram of iron oxide nanoparticles per gram of adhesive.

8. The MRI-compatible guidewire of claim 1, wherein the elongate, flexible tubular shaft comprises polyether ether ketone (PEEK).

9. The MRI-compatible guidewire of claim 1, further comprising a transition section between a distal end of the elongate, flexible tubular shaft and the distal end portion of the guidewire, wherein the transition section comprises an elongate inner tube and an elongate outer tube, wherein the inner tube comprises opposite first and second end portions and wherein the outer tube comprises opposite first and second end portions, wherein the inner tube first end portion resides within the lumen of the elongate, flexible tubular shaft at the elongate, flexible tubular shaft distal end, wherein the outer tube coaxially surrounds and is adhesively secured to the inner tube second end portion, wherein the elongate spring coil first end resides within a lumen of the outer tube at the outer tube second end portion and surrounds a portion of the inner tube second end portion, and wherein the elongate core wire extends through a lumen of the inner tube.

10. The MRI-compatible guidewire of claim 9, wherein the inner tube comprises polyimide, and wherein the outer tube comprises polyether block amide.

11. The MRI-compatible guidewire of claim 1, further comprising at least one fused silica capillary tube located within the inner lumen of the elongate, flexible tubular shaft, and wherein the first end portion of the elongate core wire is adhesively secured within the at least one fused silica capillary tube.

12. The MRI-compatible guidewire of claim 1, wherein the elongate core wire intermediate portion has a diameter of about 0.014 inch.

13. The MRI-compatible guidewire of claim 1, wherein a maximal outer diameter of the guidewire is less than or equal to 0.035 inch, and wherein the guidewire has a length of between about 2 meters (78.74 inches) and about 3 meters (118.11 inches).

14. The MRI-compatible guidewire of claim 1, wherein the guidewire has a maximum specific absorption rate (SAR) of less than 2° C. at 1 Watt/kilogram in an MRI environment at 1.5 Tesla.

15. The MRI-compatible guidewire of claim 1, wherein the first and second legs are coupled together and to the elongate spring coil via the polymeric material.

16. A guidewire for use in a magnetic resonance imaging (MRI) procedure, the guidewire comprising:

an elongate, flexible tubular shaft comprising an inner lumen;

an elongate core wire of non-ferromagnetic material comprising opposite first and second end portions, wherein the first end portion resides within the elongate, flexible tubular shaft inner lumen and is adhesively secured therewithin, and wherein the second end portion comprises a plurality of spaced-apart, passive MRI-visible markers; and an elongate spring coil of non-ferromagnetic material axially surrounding a portion of the elongate core wire, wherein the elongate spring coil comprises opposite first and second ends, wherein a distal portion of the second end portion of the elongate core wire is bent about one hundred eighty degrees (180°) to define a bent tip joining first and second legs of the distal portion of the elongate core wire, wherein the first and second legs reside inside the elongate spring coil, and wherein the elongate spring coil second end is anchored directly to the bent tip of the elongate core wire second end portion via polymeric material that forms an external rounded distal tip of the guidewire.

17. The guidewire of claim 16, wherein the elongate core wire first and second end portions are separated by an intermediate portion, wherein the intermediate portion has a round cross-section, and wherein the first and second end portions of the elongate core wire each have a non-round cross-section.

18. The guidewire of claim 16, wherein the elongate core wire comprises Nitinol, wherein the elongate spring coil comprises tungsten, and wherein the elongate, flexible tubular shaft comprises polyether ether ketone (PEEK).

19. The guidewire of claim 16, wherein the first leg merges into the bent tip corresponding to the distal portion that is bent about one hundred eighty degrees (180°) that then merges into the second leg, wherein the second leg resides adjacent the first leg of the elongate core wire, wherein the second leg comprises a free end facing the intermediate portion of the elongate core wire, and wherein the second end portion of the elongate spring coil is anchored directly to the bent tip and the first and second legs of the elongate core wire via the polymeric material.

20. The guidewire of claim 16, wherein one of the plurality of spaced apart passive MRI-visible markers is configured to define an enlarged outer diameter of the first leg of the elongate core wire adjacent and before the bent tip.

21. The guidewire of claim 16, wherein the first and second legs are parallel to each other and coupled together and to the elongate spring coil via the polymeric material.

* * * * *

UNITED STATES PATENT AND TRADEMARK OFFICE
CERTIFICATE OF CORRECTION

PATENT NO. : 10,596,353 B2
APPLICATION NO. : 15/294013
DATED : March 24, 2020
INVENTOR(S) : Flores et al.

Page 1 of 1

It is certified that error appears in the above-identified patent and that said Letters Patent is hereby corrected as shown below:

In the Specification

Column 2, Line 62:
Please add a paragraph break between the words "adhesive." and "It"

Column 3, Line 24:
Please insert a paragraph indentation before the phrase "FIG. 5"

Signed and Sealed this
Twenty-eighth Day of July, 2020

Andrei Iancu
*Director of the United States Patent and Trademark Office*